United States Patent [19]

Akita et al.

[11] 4,170,641
[45] Oct. 9, 1979

[54] 1-N-(ω-AMINOALKANESULFONYL) DERIVATIVE OF AMINOGLYCOSIDIC ANTIBIOTIC AND PROCESS FOR PREPARATION THEREOF

[75] Inventors: Eiichi Akita, Kamakura; Yukio Horiuchi, Tokyo; Takeo Miyazawa, Tokyo; Hamao Umezawa, Tokyo, all of Japan

[73] Assignee: Meiji Seika Kaisha, Ltd., Tokyo, Japan

[21] Appl. No.: 911,522

[22] Filed: Jun. 1, 1978

[30] Foreign Application Priority Data

Jun. 10, 1977 [JP] Japan .................................. 52/68005

[51] Int. Cl.$^2$ ...................... A61K 31/71; C07H 15/22
[52] U.S. Cl. ...................................... 424/180; 536/10; 536/17 R
[58] Field of Search ..................... 536/10, 17; 424/180

[56] References Cited

U.S. PATENT DOCUMENTS

| Re. 28,647 | 12/1975 | Umezawa et al. | 536/10 |
|---|---|---|---|
| 3,268,508 | 8/1966 | Sugazawa et al. | 536/10 |
| 3,925,354 | 12/1975 | Umezawa et al. | 536/17 |
| 3,965,089 | 6/1976 | Umezawa et al. | 536/10 |

Primary Examiner—Johnnie R. Brown
Attorney, Agent, or Firm—Haight & Huard

[57] ABSTRACT

A new 1-N-(ω-aminoalkanesulfonyl) derivative of an aminoglycosidic antibiotic such as ribostamycin, 3'-deoxy- or 3',4'-dideoxy-ribostamycin, kanamycin A or B, and 3'-deoxy- or 3',4'-dideoxy-kanamycin B exhibits a broader, antibacterial spectrum than the parent aminoglycosidic antibiotic and is useful in the therapeutic treatment of infections caused by gram-positive and gram-negative bacteria including drug-resistant strains thereof. The aforesaid derivative may be made by reaction between the parent antibiotic and an amino-protected ω-aminoalkanesulfonic acid halide and removal of the amino-protecting group from the condensation product.

12 Claims, No Drawings

1-N-(ω-AMINOALKANESULFONYL) DERIVATIVE OF AMINOGLYCOSIDIC ANTIBIOTIC AND PROCESS FOR PREPARATION THEREOF

BACKGROUND OF THE INVENTION

1. Field of the Invention

This invention relates to new and useful 1-N-(ω-aminoalkanesulfonyl) derivatives of aminoglycosidic antibiotics and a process for the preparation thereof.

2. Description of the Prior Art

The synthesis of 1-amino-substituted derivatives of aminoglycosidic antibiotics which are active to bacteria resistant to such aminoglycosidic antibiotics and therapeutically useful due to the presence of the substituent in the 1-amino group has been preceded by butirosins A and B which are aminoglycosidic antibiotics bearing (S)-α-hydroxy-γ-aminobutyryl substituent on the 1-amino group discovered as a fermentative product of natural origin (see U.S. Pat. No. 3,541,078 where the butirosins are referred to as ambutirosins A and B). Substantial success has been achieved by the synthesis of amikacin, 1-N-(α-hydroxy-γ-aminobutyryl) derivative of kanamycin A (U.S. Pat. No. 3,781,268 and J. Antibiotics, 25 (12), 695–708 (1972) where the derivative is designated as BB-K8). In this vein, there have been synthesized 1-amino-substituted derivatives of various aminoglycosidic antibiotics which carry an (S)-α-hydroxy-γ-aminobutyryl substituent (hereinafter referred to as L-HABA) or its homologue, an α-hydoxy-ω-aminoalkanoyl substituent as a side chain on the 1-amino group (see, for example, British Patent No. 1,426,908, U.S. Pat. No. 4,001,208 and J. Antibiotics, 26, (6) 351–357 (1973)). These substituted derivatives principally fall within the category of 1-N-(S)-α-substituted-ω-aminoalkanecarboxylic acid derivatives. A new type of side chain which the parent aminoglycosidic antibiotics should carry as a substituent on the 1-amino group and which is effective to improve the antibacterial properties of the parent antibiotics had not been discovered until 1-N-ethylsisomicin was successfully prepared by a semi-synthetic process.

SUMMARY OF THE INVENTION

We have synthesized various new derivatives of aminoglycosidic antibiotics containing a 2-deoxystreptamine moiety in the molecule and checked screened them in to search for new substances which exhibit wide antibacterial spectra against drug-resistant bacteria and *Pseudomonas* sp. As a consequence, we have now found that the introduction of a 1-N-(ω-aminoalkanesulfonyl) side chain into an aminoglycosidic antibiotic effects considerable extension of the range of the antibacterial spectrum thereof against drug-resistant bacteria and *Pseudomonas* sp. without reducing the antibacterial activity of the parent antibiotic.

DETAILED DESCRIPTION OF THE INVENTION

According to a first aspect of this invention, therefore, there is provided a 1-N-(ω-aminoalkanesulfonyl) derivative of aminoglycosidic antibiotics having the general formula:

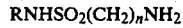

$$RNHSO_2(CH_2)_nNH_2 \qquad (I)$$

or a pharmaceutically acceptable salt thereof, wherein RNH— represents the residue of an aminoglycosidic antibiotic comprising a 2-deoxystreptamine moiety in its molecule, the nitrogen atom shown in the residue RNH— being bonded to the carbon atom at the 1-position of the 2-deoxystreptamine moiety, and n represents an integer of 2, 3 or 4. Alternatively, the residue RNH— may be defined as the moiety which is present in said aminoglycosidic antibiotic molecule and which remains after the removal of one hydrogen atom from the 1-amino group of the 2-deoxystreptamine moiety of said aminoglycosidic antibiotic molecule.

It is generally believed that the antibacterial activity of the aminoglycosidic antibiotics is attributed to the amino groups present in their molecule, and also that if even a part of the amino groups existing in an aminoglycosidic antibiotic is chemically modified, for example, by acylation in order to lose its basic character, then the antibacterial activity of the modified aminoglycosidic antibiotic substantially decreases to an appreciable extent. In the aforementioned cases of butirosin and amikacin, the acylation of the 1-amino group, on the one hand, eliminates its basic character and, on the other hand, provides another amino group at the ω-position of the side chain, so that the balance of the basic character in the entire compound is believed to remain substantially unchanged. Thus, these cases may not constitute exceptions to the common knowledge that acylation in order to lose the basic character will result in noticeable reduction in antibacterial activity. With 1-N-ethylsisomicin, the basic character of the 1-amino group inherently remains unchanged.

In the new 1-N-(ω-aminoalkanesulfonyl) derivatives provided in accordance with this invention, however, it is thought that the balance of the basic character in the entire molecule will be negative despite the additional presence of the amino group at the ω-position as it is well known that an NH proton in the sulfonamide linkage renders the same acidic in nature (see, for example, Fieser & Fieser "Advanced Organic Chemistry" P. 507, Reinhold-Maruzen (1961)). Thus, aqueous solutions of the new derivatives actually show a lower pH value than those of the parent antibiotics at the same concentration. Contrary to the prospect that the new derivatives of the above formula (I) according to the invention would exhibit a considerably lower antibacterial activity than do the parent antibiotics, they, in fact have unexpected advantages in that they show an extended antibacterial spectrum against drug-resistant strains and *Pseudomonas* sp. while retaining the high antibacterial activity of the parent antibiotics.

Among the known 1-N-ω-aminoalkanoyl derivatives of aminoglycosidic antibiotics, those which retain the antibacterial activity of the parent antibiotics and which are effective against resistant strains and *Pseudomonas* sp. are carrying an optically active aminoalkanoyl side chain containing a hydroxyl group in the (S)-configuration on the α-carbon atom of said side chain, except for those few derivatives which include 1-N-D-isoserylkanamycin A (J. Antibiotics, 27 (1), 90–93 (1974) and U.S. Pat. No. 3,939,143) and 1-N-D-HABA-kanamycin A denoted as BB-K 31 (J. Antibiotics, 26 (5), 297–301 (1973)). However, the 1-N-(ω-aminoalkanesulfonyl) group present in the new derivatives of the formula (I) is essentially optically inactive. It was accordingly unexpected that the introduction of the optically inactive group as side-chain into the 1-amino group would result in the derivatives having an extended antibacterial spectrum. Further, neither complicated asymmetric synthesis nor optical resolution is necessary for the reagent used to introduce the (ω-aminoalkanesulfonyl) group, which is advantageous in preparing the compounds of the formula (I) according to this invention.

Examples of the residual group RNH— in the general formula (I) described hereinabove include aminoglycosyl residues of kanamycins A, B and C, neomycins A, B and C, paromamine, paromomycins I and II, ribostamycin, lividomycins A and B, gentamicins A and C, and deoxy-derivatives thereof.

Particular examples of the residue RNH— are as follows:

(i) Ribostamycin residue having the formula

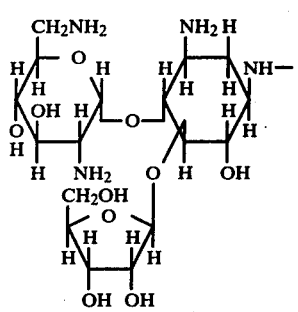

(ii) Kanamycin A residue having the formula

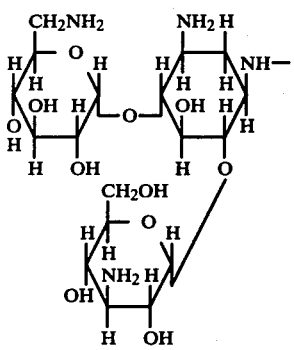

(iii) Kanamycin B residue having the formula

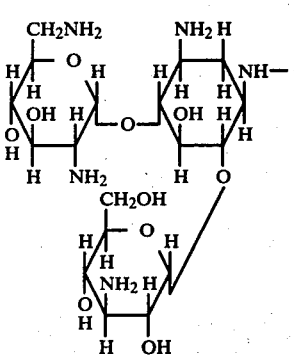

(iv) 3'-Deoxyribostamycin residue having the formula

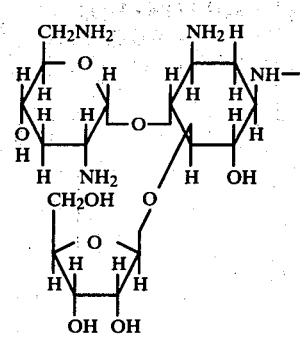

(v) 3',4'-Dideoxyribostamycin residue having the formula

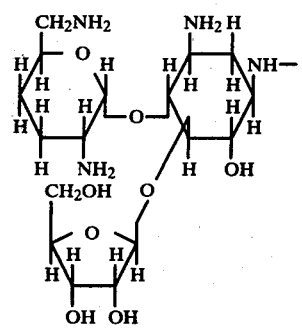

(vi) 3'-Deoxykanamycin B residue having the formula

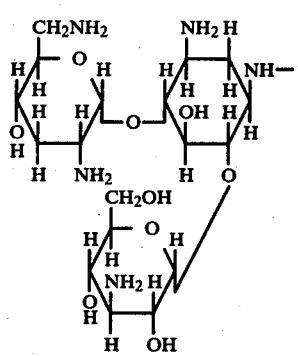

(vii) 3',4'-Dideoxykanamycin B residue having the formula

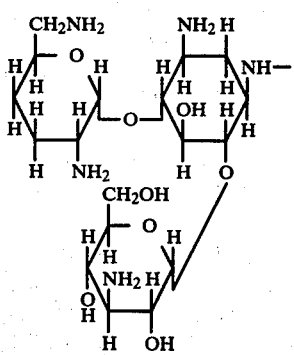

Examples of the ω-aminoalkanesulfonyl group —$SO_2(CH_2)_nNH_2$ include the 2-aminoethanesulfonyl, 3-aminopropanesulfonyl and 4-aminobutanesulfonyl group.

Specific examples of the compounds of the invention corresponding to the formula (I) include the 1-N-(2-aminoethanesulfonyl) derivative, 1-N-(3-aminopropanesulfonyl) derivative and 1-N-(4-aminobutanesulfonyl) derivative of each of the antibiotics of the general formula:

$$R-NH_2 \quad (II)$$

which may be kanamycin A, 3'-deoxykanamycin A, 3'-deoxykanamycin B, 3',4'-dideoxykanamycin B (namely dibekacin), kanamycin C, 3'-deoxykanamycin C, 3',4'-dideoxykanamycin C, neomycin A, 3'-deoxy- or 3',4'-dideoxy-neomycin A, paromamine, paromomycins I and II, ribostamycin, 3'-deoxy- or 3',4'-dideoxy-ribostamycin, lividomycins A and B and gentamicins A and C, for example.

Examples of pharmaceutically acceptable salts of the compounds according to this invention include the hydrochloride, sulfate, phosphate, acetate, maleate, fumarate, succinate, tartrate, oxalate, citrate, methanesulfonate, ethanesulfonate and the like.

Experiments have shown that the 1-N-(ω-aminoalkanesulfonyl) derivatives of the invention possess a significantly improved antibacterial activity as compared to the corresponding 1-N-(α-hydroxy-ω-aminobutyryl) derivatives against certain strains of bacteria which are specified depending on the nature of the parent antibiotics.

Minimum inhibitory concentrations (M.I.C. expressed in mcg/ml) of the novel compounds (I) of the invention against various bacteria were determined by the standard serial dilution method using agar culture medium at 37° C., an evaluation being made 17 hours after incubation. The results are listed in Table 1 below where M.I.C. of the parent antibiotics are also shown by way of comparison.

In Table 1 below, the following abbreviations or designations are used:

Compound No. 1: 1-N-(2-Aminoethanesulfonyl)kanamycin A
Compound No. 2: 1-N-(3-Aminopropanesulfonyl)kanamycin A
Compound No. 3: 1-N-(4-Aminobutanesulfonyl)kanamycin A
Compound No. 4: 1-N-(2-Aminoethanesulfonyl)kanamycin B
Compound No. 5: 1-N-(3-Aminopropanesulfonyl)kanamycin B
Compound No. 6: 1-N-(2-Aminoethanesulfonyl)-3'-deoxykanamycin B
Compound No. 7: 1-N-(2-Aminoethanesulfonyl)dibekacin (that is, 1-N-(2-aminoethanesulfonyl)-3',4'-dideoxykanamycin B)
Compound No. 8: 1-N-(3-Aminopropanesulfonyl)dibekacin
Compound No. 9: 1-N-(2-Aminoethanesulfonyl)ribostamycin
Compound No. 10: 1-N-(2-Aminoethanesulfonyl)-3'-deoxyribostamycin
Compound No. 11: 1-N-(2-Aminoethanesulfonyl)-3',4'-dideoxyribostamycin
Amikacin: 1-N-(L-2-hydroxy-4-aminobutyryl)kanamycin A
BB-K26: 1-N-(L-2-hydroxy-4-aminobutyryl)kanamycin B
L-HABA-RBS: 1-N-(L-2-hydroxy-4-aminobutyryl)-ribostamycin (Butirosin B)
L-HABA-DRBS: 1-N-(L-2-hydroxy-4-aminobutyryl)-3'-deoxyribostamycin Table 1a

| Test organisms | Compound No. 1 | Compound No. 2 | Compound No. 3 | Kanamycin A (comparative) | Amikacin (comparative) |
|---|---|---|---|---|---|
| Incubation on nutrient agar | | | | | |
| Staphylococcus aureus 209P | 6.25 | 25 | 100 | 0.78 | 1.56 |
| Escherichia coli NIHJ | 6.25 | 12.5 | 100 | 1.56 | — |
| Escherichia coli K-12 | 3.12 | 12.5 | 100 | 1.56 | 0.78 |
| Escherichia coli K-12 ML1410 | — | — | — | — | — |
| Escherichia coli K-12 ML1629 | 6.25 | 25 | 100 | >100 | 0.78 |
| Escherichia coli K-12 ML1630 | 6.25 | 50 | >100 | >100 | 1.56 |
| Escherichia coli K-12 ML1410 R81 | 6.25 | 100 | >100 | >100 | 1.56 |
| Escherichia coli K-12 LA290 R55 | 6.25 | 50 | >100 | 100 | 0.78 |
| Escherichia coli K-12 LA290 R56 | 3.12 | 25 | 100 | 12.5 | 0.39 |
| Escherichia coli K-12 La290 R64 | 1.56 | 25 | 100 | — | 0.78 |
| Escherichia coli JR66/W677 | 6.25 | — | — | >100 | 3.12 |
| Escherichia coli K-12 J5 R11-2 | 3.12 | 25 | 100 | — | — |
| Klebsiella pneumoniae 22 # 3038 | 12.5 | 100 | >100 | >100 | — |
| Mycobacterium smegmatis 607 | 25 | — | — | 0.78 | — |
| Pseudomonas aeruginosa A3 | 3.12 | 25 | 100 | 50 | 3.12 |
| Pseudomonas aeruginosa No. 12 | 12.5 | 100 | >100 | 25 | 6.25 |
| Pseudomonas aeruginosa H9 | 25 | >100 | >100 | >100 | — |
| Pseudomonas aeruginosa Ti-13 | 25 | 100 | >100 | >100 | 3.12 |
| Pseudomonas aeruginosa 99 | 25 | >100 | >100 | >100 | 12.5 |
| Pseudomonas aeruginosa H11 | 25 | >100 | >100 | — | 25 |
| Incubation on Müller-Hinton agar | | | | | |
| Staphylococcus aureus Smith S-424 | 0.39 | — | — | 0.39 | 0.39 |
| Staphylococcus aureus 209P JC-1 | — | — | — | — | — |
| Staphylococcus aureus N-0003 | — | — | — | — | — |
| Staphylococcus aureus C-73-10 | — | — | — | — | — |
| Staphylococcus epidermidis N-0015 | 0.10 | — | — | 0.10 | 0.20 |
| Escherichia coli K-12 IAM 1264 | 1.56 | — | — | 0.39 | 0.39 |
| Escherichia coli A-0001 | 6.25 | — | — | 3.13 | 1.56 |
| Salmonella D-0006 | 6.25 | — | — | 1.56 | 0.78 |
| Proteus vulgaris OX19 | 1.56 | — | — | 1.56 | 0.78 |
| Proteus mirabilis J-0006 | 0.78 | — | — | 0.39 | 0.78 |
| Pseudomonas aeruginosa IAM 1007 | 1.56 | — | — | 25 | 1.56 |
| Pseudomonas aeruginosa M-0002 | 3.13 | — | — | 50 | 3.13 |

Table 1a-continued

| Test organisms | Compound No. 1 | Compound No. 2 | Compound No. 3 | Kanamycin A (comparative) | Amikacin (comparative) |
|---|---|---|---|---|---|
| *Pseudomonas aeruginosa* M-0025 | 0.78 | — | — | 12.5 | 3.13 |
| *Staphylococcus albus* PCI 1200A | — | — | — | — | — |
| *Streptococcus faecalis* ATCC 8043 | 12.5 | — | — | — | 25 |
| *Bacillus anthracis* | 0.10 | — | — | — | 0.20 |

Table 1b

| Test Organisms | Compound No. 4 | Compound No. 5 | Kanamycin B (comparative | BB-K26 (comparative) | Compound No. 6 | 3'-Deoxy-kanamycin B (comparative) |
|---|---|---|---|---|---|---|
| Incubation on nutrient agar | | | | | | |
| *Staphylococcus aureus* 209P | <0.39 | 3.12 | 0.39 | 0.78 | 6.25 | — |
| *Escherichia coli* NIHJ | 1.56 | 3.12 | 0.78 | 0.78 | 12.5 | — |
| *Escherichia coli* K-12 | 1.56 | 3.12 | 0.78 | 0.78 | 6.25 | — |
| *Escherichia coli* K-12 ML1410 | 1.56 | — | — | 3.13 | — | — |
| *Escherichia coli* K-12 ML1629 | 3.12 | 6.5 | >100 | 1.56 | 12.5 | — |
| *Escherichia coli* K-12 ML1630 | 3.12 | 3.12 | >100 | 1.56 | 25 | 1.56 |
| *Escherichia coli* K-12 ML1410 R81 | 3.12 | 6.25 | >100 | 1.56 | 12.5 | — |
| *Escherichia coli* K-12 LA290 R55 | 3.12 | 3.12 | 12.5 | 1.56 | 12.5 | 50 |
| *Escherichia coli* K-12 LA290 R56 | 1.56 | 3.12 | 3.13 | 0.39 | 12.5 | — |
| *Escherichia coli* K-12 La290 R64 | 1.56 | 3.12 | 3.13 | 0.39 | 6.25 | — |
| *Escherichia coli* JR66/W677 | 6.25 | 50 | >100 | 3.13 | — | 50 |
| *Escherichia coli* K-12 J5 R11-2 | 1.56 | 1.56 | — | — | 12.5 | — |
| *Klebsiella pneumoniae* 22 # 3038 | 12.5 | 50 | >100 | 6.25 | 25 | 50 |
| *Mycobacterium smegmatis* 607 | 6.25 | 12.5 | 0.78 | 0.78 | — | — |
| *Pseudomonas aeruginosa* A3 | 1.56 | 6.25 | 50 | 6.25 | 6.25 | — |
| *Pseudomonas aeruginosa* No. 12 | 12.5 | 25 | 12.5 | 6.25 | 100 | — |
| *Pseudomonas aeruginosa* H9 | 25 | >100 | — | 25 | >100 | — |
| *Pseudomonas aeruginosa* TI-13 | 25 | 25 | 100 | 25 | 100 | — |
| *Pseudomonas aeruginosa* 99 | 25 | 50 | >100 | 25 | >100 | — |
| *Pseudomonas aeruginosa* H11 | 12.5 | 100 | — | — | >100 | — |
| Incubation on Müller-Hinton agar | | | | | | |
| *Staphylococcus aureus* Smith S-424 | 0.20 | 0.78 | 0.20 | — | — | — |
| *Staphylococcus aureus* 209P JC-1 | — | — | — | — | — | — |
| *Staphylococcus aureus* N-0003 | — | — | — | — | — | — |
| *Staphylococcus aureus* C-73-10 | — | — | — | — | — | — |
| *Staphylococcus epidermidis* N-0015 | 0.10 | 0.78 | 0.025 | — | — | — |
| *Escherichia coli* K-12 IAM 1264 | 0.78 | 1.56 | 0.20 | — | — | — |
| *Escherichia coli* A-0001 | 3.13 | 6.25 | 1.56 | — | — | — |
| *Salmonella* D-0006 | 3.13 | 12.5 | 0.78 | — | — | — |
| *Proteus vulgris* OX19 | 1.56 | 3.13 | 0.20 | — | — | — |
| *Proteus mirabilis* J-0006 | 0.78 | 1.56 | 0.20 | — | — | — |
| *Pseudomonas aeruginosa* IAM 1007 | 1.56 | 3.13 | 3.13 | — | — | — |
| *Pseudomonas aeruginosa* M-0002 | 3.13 | 6.25 | 25 | — | — | — |
| *Pseudomonas aeruginosa* M-0025 | 3.13 | 6.25 | 6.25 | — | — | — |
| *Staphylococcus albus* PCI 1200A | — | — | — | — | — | — |
| *Streptococcus faecalis* ATCC 8043 | — | — | — | — | — | — |
| *Bacillus anthracis* | — | — | — | — | — | — |

Table 1c

| Test organisms | Compound No. 7 | Compound No. 8 | Dibekacin (comparative) | Compound No. 9 | Ribostamycin (comparative) | L-HABA-RBS (comparative) |
|---|---|---|---|---|---|---|
| Incubation on nutrient agar | | | | | | |
| *Staphylococcus aureus* 209P | 3.12 | 6.25 | — | 6.25 | 3.12 | 6.25 |
| *Escherichia coli* NIHJ | 12.5 | 25 | — | 3.12 | 3.12 | — |
| *Escherichia coli* K-12 | 12.5 | 25 | — | 1.56 | 3.12 | 1.56 |
| *Escherichia coli* K-12 ML1410 | — | — | — | 1.56 | — | 3.12 |
| *Escherichia coli* K-12 ML1629 | 12.5 | 25 | — | 25 | >100 | 6.25 |
| *Escherichia coli* K-12 ML1630 | 50 | 25 | 1.56 | 3.12 | — | 6.25 |
| *Escherichia coli* K-12 ML1410 R81 | 25 | 25 | — | 3.12 | >100 | 6.25 |
| *Escherichia coli* K-12 LA290 R 55 | 50 | 50 | 100 | 3.12 | — | 3.12 |
| *Escherichia coli* K-12 LA290 R 56 | 12.5 | 25 | — | 3.12 | 3.12 | 3.12 |
| *Escherichia coli* K-12 LA290 R 64 | 12.5 | 12.5 | — | 1.56 | — | 3.12 |
| *Escherichia coli* JR66/W677 | 50 | 50 | 50 | >100 | >100 | >100 |
| *Escherichia coli* K-12 J5 R11-2 | 6.25 | 12.5 | — | 1.56 | — | — |
| *Klebsiella pneumoniae* 22 # 3038 | 50 | 50 | 100 | >100 | >100 | >100 |
| *Mycobacterium smegmatis* 607 | 12.5 | 3.12 | — | 6.25 | 6.25 | 1.56 |
| *Pseudomonas aeruginosa* A3 | 6.25 | 12.5 | — | 12.5 | >100 | 25 |
| *Pseudomonas aeruginosa* No. 12 | 25 | 100 | — | 100 | >100 | 12.5 |
| *Pseudomonas aeruginosa* H9 | >100 | 100 | — | >100 | >100 | 6.25 |
| *Pseudomonas aeruginosa* TI-13 | >100 | 50 | — | >100 | >100 | 100 |
| *Pseudomonas aeruginosa* 99 | >100 | >100 | — | >100 | >100 | >100 |
| *Pseudomonas aeruginosa* H11 | >100 | >100 | — | >100 | — | 50 |
| Incubation on Müller-Hinton agar | | | | | | |

Table 1c-continued

| Test organisms | Compound No. 7 | Compound No. 8 | Dibekacin (comparative) | Compound No. 9 | Ribostamycin (comparative) | L-HABA-RBS (comparative) |
|---|---|---|---|---|---|---|
| Staphylococcus aureus Smith S-424 | — | — | — | 1.56 | 0.78 | 0.78 |
| Staphylococcus aureus 209P JC-1 | — | — | — | 0.39 | — | 0.78 |
| Staphylococcus aureus N-0003 | — | — | — | 1.56 | — | 3.13 |
| Staphylococcus aureus C-73-10 | — | — | — | 1.56 | — | 3.13 |
| Staphylococcus epidermidis N-0015 | — | — | — | 0.78 | 0.78 | 0.78 |
| Escherichia coli K-12 IAM 1264 | — | — | — | 1.56 | 0.78 | 1.56 |
| Escherichia coli A-0001 | — | — | — | 3.13 | 3.13 | 3.13 |
| Salmonella D-0006 | — | — | — | 12.5 | 6.25 | 12.5 |
| Proteus vulgaris OX19 | — | — | — | 3.13 | 0.78 | 1.56 |
| Proteus mirabilis J-0006 | — | — | — | 1.56 | 0.39 | 1.56 |
| Pseudomonas aeruginosa IAM 1007 | — | — | — | 25 | 50 | 12.5 |
| Pseudomonas aeruginosa M-0002 | — | — | — | 100 | >100 | 50 |
| Pseudomonas aeruginosa M-0025 | — | — | — | 100 | 50 | 50 |
| Staphylococcus albus PCI 1200A | — | — | — | 0.39 | — | 0.78 |
| Streptococcus faecalis ATCC 8043 | — | — | — | — | — | — |
| Bacillus anthracis | — | — | — | — | — | — |

Table 1d

| Test organisms | Compound No. 10 | 3'-Deoxyribostamycin (comparative) | L-HABA-DRBS (comparative) | Compound No. 11 | 3',4'-Dideoxy ribostamycin (comparative) |
|---|---|---|---|---|---|
| Incubation on nutrient agar | | | | | |
| Staphylococcus aureus 209P | 3.12 | 0.39 | 0.78 | 50 | 12.5 |
| Escherichia coli NIHJ | 3.12 | 1.56 | 1.56 | 25 | 12.5 |
| Escherichia coli K-12 | 3.12 | 0.78 | 0.78 | 12.5 | 6.25 |
| Escherichia coli K-12 ML1410 | — | — | — | — | — |
| Escherichia coli K-12 ML1629 | 3.12 | 50 | 0.78 | 25 | >100 |
| Escherichia coli K-12 ML1630 | 6.25 | >100 | 1.56 | 25 | >100 |
| Escherichia coli K-12 ML1410 R81 | 6.25 | >100 | 3.12 | 50 | — |
| Escherichia coli K-12 LA290 R55 | 6.25 | 1.56 | 1.56 | 25 | 12.5 |
| Escherichia coli K-12 LA290 R56 | 3.12 | 0.78 | 0.78 | 25 | — |
| Escherichia coli K-12 LA290 R64 | 3.12 | 0.39 | 0.78 | 25 | — |
| Escherichia coli JR66/W677 | 6.25 | 3.12 | 3.12 | — | 12.5 |
| Escherichia coli K-12 J5 R11-2 | 1.56 | 50 | 0.39 | 25 | — |
| Klebsiella pneumoniae 22 # 3038 | 12.5 | 3.12 | 3.12 | 50 | — |
| Mycobacterium smegmatis 607 | 3.12 | 0.39 | 0.39 | — | 3.12 |
| Pseudomonas aeruginosa A3 | 6.25 | 0.78 | 3.12 | 100 | 6.25 |
| Pseudomonas aeruginosa No. 12 | 50 | 6.25 | 25 | >100 | 25 |
| Pseudomonas aeruginosa H9 | 50 | 6.25 | 25 | >100 | — |
| Pseudomonas aeruginosa TI-13 | 50 | 3.12 | 25 | >100 | 25 |
| Pseudomonas aeruginosa 99 | 100 | 6.25 | 25 | >100 | 50 |
| Pseudomonas aeruginosa H11 | 100 | 6.25 | 50 | >100 | — |
| Incubation on Müller-Hinton agar | | | | | |
| Staphylococcus aureus Smith S-424 | 0.78 | — | — | — | — |
| Staphylococcus aureus 209P JC-1 | — | — | — | — | — |
| Staphylococcus aureus N-0003 | — | — | — | — | — |
| Staphylococcus aureus C-73-10 | — | — | — | — | — |
| Staphylococcus epidermidis N-0015 | 0.78 | — | — | — | — |
| Escherichia coli K-12 IAM 1264 | 1.56 | 1.56 | 1.56 | — | — |
| Escherichia coli A-0001 | 3.13 | — | — | — | — |
| Salmonella D-0006 | 12.5 | — | — | — | — |
| Proteus vulgaris OX19 | 1.56 | — | — | — | — |
| Proteus mirabilis J-0006 | 1.56 | — | — | — | — |
| Pseudomonas aeruginosa IAM 1007 | 1.56 | 1.56 | 0.78 | — | — |
| Pseudomonas aeruginosa M-0002 | 12.5 | — | — | — | — |
| Pseudomonas aeruginosa M-0025 | 2.5 | — | — | — | — |
| Staphylococcus albus PCI 1200A | — | — | — | — | — |
| Streptococcus faecalis ATCC 8043 | — | — | — | — | — |
| Bacillus anthracis | — | — | — | — | — |

As will be clear from the antibacterial spectra shown in Table 1, the compounds of the invention exhibit a high antibacterial activity against various gram-positive and gram-negative bacteria including Staphylococcus, Escherichia coli and Pseudomonas aeruginosa and resistant strains thereof. It has also been observed that the present compounds show a lower acute toxicity than that of the parent antibiotics. For instance the Compound 4 monosulfate shows $LD_{50}$ value of more than 200 mg/kg, the Compound 9 monosulfate, about 500 mg/kg and the Compound 1 (free base) about 800 mg/kg when intravenously injected into mice.

Accordingly, the novel compounds of the invention are useful in the treatment of infectious diseases caused by gram-positive and gram-negative bacteria. For this purpose, the new compounds of this invention and their pharmaceutically acceptable acid-addition salts may be administered orally, intraperitoneally, intravenously, subcutaneously or intramuscularly using any pharmaceutical form known in the art for such administration and in manner similar to the administration of known kanamycins. For instance, the new compounds of the formula (I) of this invention may be administered orally using any pharmaceutical dosage form known in the art for oral administration. Examples of the pharmaceutical dosage forms for oral administration are powders, capsules, tablets, syrup and the like. A suitable dose of the new compounds of this invention for effective treatment of bacterial infections lies in a range of 0.1 to 2 g per person a day when it is given orally. It is preferred that said dose should be orally administered in three to four aliquots per day. The new compounds of this invention may also be administered by intramuscular injection at a dosage of 50 to 1000 mg per person two to four times per day. Moreover, the new compounds of this invention may be formulated into an ointment for external application which contains a compound of this invention at a concentration of 0.5–5% by weight in mixture with a known ointment base such as polyethylene glycol. Furthermore, the new compound of this invention is useful for sterilization of surgical instruments.

According to a second aspect of this invention, therefore, there is provided an antibacterial composition comprising as the active ingredient an antibacterially effective amount of a 1-N-(ω-aminoalkanesulfonyl) derivative of an aminoglycosidic antibiotic having the general formula (I) as defined hereinbefore, in combination with a pharmaceutically acceptable carrier for the active ingredient.

According to a third aspect of this invention there is provided a method of therapeutically treating a bacterial infection in an animal, including humans, which comprises administering to the host of the bacterial infection an antibacterially effective amount of a 1-N-(ω-aminoalkanesulfonyl) derivative of an aminoglycosidic antibiotic having the general formula (I) as defined hereinbefore, in order to inhibit the growth of bacteria.

According to a further aspect of this invention, there is provided a process for the preparation of a 1-N-(ω-aminoalkanesulfonyl) derivative of an aminoglycosidic antibiotic having the general formula:

$$RNHSO_2(CH_2)_nNH_2 \qquad (I)$$

wherein RNH— represents the residue of an aminoglycosidic antibiotic comprising the 2-deoxystreptamine moiety in its molecule, the nitrogen atom in the residue RNH— being bonded to the carbon atom at the 1-position of the 2-deoxystreptamine moiety, and n is 2, 3 or 4. The process comprises reacting an aminoglycosidic antibiotic of the general formula:

$$\underset{H}{\overset{RNH}{|}} \qquad (II)$$

wherein RNH- is as defined above, with an ω-aminoalkanesulfonic acid halide of the general formula:

$$XSO_2(CH_2)_nNH.A \qquad (III)$$

wherein X represents a halogen atom, such as chlorine or bromine, A represents an amino-protecting group and n is as defined above, and then removing the amino-protecting group A from the resultant condensation product in a known manner.

The process according to this invention may be carried out by any reaction technique known per se and generally employed in treating hydrophilic substances. The starting aminoglycosidic antibiotic (II) may be used in the form of a free base or its acid addition salt. If desired, an amino group or amino groups other than the 1-amino group and part or all of the hydroxyl groups existing in the aminoglycosidic antibiotic may be blocked with known protective groups.

The amino-protecting group A in the sulfonic acid halide (III) to be condensed with the 1-amino group of the starting material (II) may be any known amino-protecting group, provided that it will not be removed in the course of the preparation of the compound (III) and during the condensation reaction with the starting material (II) and that it can be removed from the condensation product under conditions which will not decompose the glucoside and the sulfonamide linkages involved in the condensation product. We prefer to use a trihaloacetyl group, particularly a trichloroacetyl or trifluoroacetyl group as the amino-protecting group A since it is adaptable to the process of the invention and removable from the condensation product by the simple procedure of treating said condensation product with concentrated aqueous ammonia.

The condensation reaction may be conveniently carried out by dissolving the starting material (II) or its salt and the reactant (III) in a suitable inert solvent, for example, methanol, tetrahydrofuran, dimethylformamide or water-dimethylformamide mixture, in the presence or absence of an acid binding agent such as a lower trialkylamine, eg. triethylamine. The reaction may be effected at ambient temperature or an elevated temperature.

In the course of the condensation raction, the sulfonic acid halide (III) will react on the other free amino group(s), if any, of the starting compound (II) as well as on the 1-amino group so that the condensation product may be in the form of a mixture comprising the desired mono-1-N-(protected-ω-aminoalkanesulfonyl) derivative and the undesired, other mono-N-(protected-ω-aminoalkanesulfonyl) derivatives, di-N-(protected-ω-aminoalkanesulfonyl) derivatives and other related derivatives. The mixed condensation products may be purified chromatographically to isolate the desired mono-1-N-(proteced-ω-aminoalkanesulfonyl) derivative, followed by removing the amino-protecting group A from the latter. It is convenient, however, to subject the mixed condensation products to the step of removing the amino-protecting group A, followed by chromatographic purification to isolate the desired 1-N-(ω-aminoalkanesulfonyl) derivative.

In order to produce the object compound (I) easily and with a reduced number of operations according to the process of the invention, the following procedure may be conveniently employed: A starting compound (II) (the free base form) is dissolved in a mixture of water and dimethylformamide, or is alternatively converted into its soluble salt and then dissolved in methanol, tetrahydrofuran or dimethyl formamide. To the solution is added triethylamine, followed by dropwise addition of a solution of a reagent ω-trihaloacetylaminoalkanesulfonyl halide (III) in dimethylformamide, methanol or tetrahydrofuran. The resultant mixture is agitated at ambient temperature over night, whereupon water and conc. aqueous ammonia are successively added to the reaction mixture. The mixture is warmed to effect the removal of the trihaloacetyl group (the amino-protecting group) and the reaction solution is then concentrated to dryness. The residue is taken up in a small amount of water and the solution is passed through a column of a strong anion-exchange resin such as Dowex 1x2 (OH−) (a product of Dow Chemical Co., U.S.A.) to adsorb thereon the mixed products including the object compound, which is followed by elution with a dilute acid such as aqueous acetic acid. The mixture thus obtained is adsorbed on a weak cation-exchange resin of carboxylic type such as Amberlite CG-50 ($NH_4^+$) (a product of Rohm & Haas Co., U.S.A.) and eluted with dilute aqueous ammonia to collect fractions containing the object compound (I). If necessary, further purification may be conducted by column chromatography on silica gel.

Trifluoro (or trichloro) acetylaminoethane sulfonic acid chloride is a preferred example of the reactant (III) to be used in the present process and may be prepared, for example, by reacting potassium or sodium aminoethanesulfonate with trifluoro (or trichloro) acetic anhydride in methanol and treating the potassium or sodium trifluoro (or trichloro) acetylaminoethanesulfonate obtained with phosphorus pentachloride ($PCl_5$) in benzene. Trifluoroacetylaminoethanesulfonic acid chloride is a pale brown crystalline product having a low melting point of 37°–38° C. The homologuous, trifluoro (or trichloro) acetylaminopropane (or butane) sulfonic acid chloride may be prepared in the same way as above but starting from potassium or sodium aminopropane (or butane) sulfonate.

This invention is further illustrated but not limited by the following Examples.

EXAMPLE 1

Kanamycin A (free base) (3000 mg; 6.2 milimoles) was dissolved in a mixture of 8 ml of water and 8 ml of dimethylformamide, to which was then added 1.4 ml (10.1 milimoles) of triethylamine. The mixture was retained at a temperature of 0°–5° C. with ice cooling under agitation, whereupon an ice-cooled solution of 3300 mg (13.7 milimoles) of N-trifluoroacetyltaurine chloride, namely trifluoroacetyl-2-aminoethanesulfonyl chloride in 11 ml of dimethylformamide was added dropwise under vigorous stirring over a period of 5–10 minutes. The stirring was continued at a temperature of 0°–5° C. for one additional hour and then at room temperature for 22 more hours, followed by the addition of 80 ml of water to decompose the remaining reagents. The resultant reaction solution indicated pH 5.8.

Conc. aqueous ammonia (12 ml) was added to the reaction solution and the mixture was warmed in a water bath at 70° C. for one hour to remove the trifluoroacetyl group from the intermediate product. After the reaction was completed, the reaction solution (about 120 ml) was directly pass through a column of 100 ml of a strong anion-exchange resin (available under trade name "Dowex 1×2" ($OH^-$ form) from Dow Chemical Co., U.S.A.). The resin column was eluted with water to give eluate fraction Nos. 1–36 and then with 0.2% aqueous acetic acid to give fraction Nos. 37–90. These fractions were each collected in 15 ml volume. The fraction Nos. 13–25 together contained about 1.5 g of unreacted kanamycin A, while the fraction Nos. 62–80 together contained about 2 g of a mixture of N-(2-aminoethanesulfonyl) derivatives of kanamycin A and a portion of the free taurine resulting from the taurine chloride reactant.

The latter fractions were taken up in 40 ml of water and then passed through a column of 100 ml of a weak cation-exchange resin of carboxylic type (available under trade name "Amberlite CG 50" ($NH_4^+$ form) from Rohm & Haas Co., U.S.A.) at a pH of 9–10. The column was eluted with water to yield eluate fraction Nos. 1–39 and then with a conc. ammonia-water (1:250 by volume) mixture to yield fractions each Nos. 40–107, these fraction being collected in 15 ml volumes. The eluate fraction Nos. 78–85 were combined together and concentrated to dryness to yield about 500 mg of a primary crude product of 1-N-(2-aminoethanesulfonyl) kanamycin A.

The crude product was taken up in 20 ml of a solvent mixture of n-butanol-ethanol-chloroform-17% aqueous ammonia (4:5:2:5 by volume) and the solution was passed through a column of 50 g (120 ml) of silica gel (available under the trade name "Wakogel C-200" from Wakojunyaku K.K., Japan) impregnated with said solvent mixture. The column was then eluted with said solvent mixture and the eluate was collected in 10 ml fractions. The fraction Nos. 35–43 were not combined together, each fraction was successively passed through a second column of the same silica gel and the column was likewise eluted. The eluate fraction Nos. 30–49 as obtained from this chromatography were again subjected to a similar chromatography. The eluate was again collected in 10 ml fractions, and the fractions 27–39 were collected and combined together, followed by the concentration to give 260 mg of a solid. The solid was dissolved in 7 ml of the same solvent mixture, passed through a column of the same silica gel and eluted with the same solvent as described above. The eluate was collected in 10 ml fractions and the fraction Nos. 29–43 were combined together and concentrated to dryness to yield 206 mg of a secondary crude product of 1-N-(2-aminoethanesulfonyl) kanamycin A.

This product was taken up in 4 ml of water and the solution was passed through a column of 20 ml of Amberlite CG 50 ($NH_4^+$ form, pH 9–10). The column was eluted with water to give eluate fraction Nos. 1–50 and then with a mixture of conc. ammonia-water (1:250 by volume) to give fraction Nos. 51–136, these fractions being collected each in 3 ml volume. The fraction Nos. 85–104 were combined and directly passed through a column of 20 ml of Dowex 1×2 ($OH^-$ form). The column was eluted with water to give fraction Nos. 1–63 and then with 0.05% aqueous acetic acid to give fraction Nos. 64–309, the eluate being collected in 3 ml volume for each of the fraction Nos. 1–114, 9 ml for Nos. 115–201 and 3 ml for Nos. 202–309. The fraction Nos. 243–266 were combined together and concentrated to dryness to yield 79.8 mg of 1-N-(2-aminoethanesulfonyl) kanamycin A. By operations similar to those described above, 57.1 mg of further 1-N-(2-aminoethanesulfomyl) kanamycin A was obtained from the fore-cut and tail-cut fractions in each of the elution phases. Total yield 136.9 mg (2.32 milimoles, 3.7%).

1-N-(2-aminoethanesulfonyl) kanamycin A, which is in the form of a colorless powder, has no definite melting point but decomposes and blackens at temperatures of 180°–242° C. This product shows an optical rotation of $[\alpha]_D^{23} = +154°$ (c=0.57 in water) and its rotatory dispersion gives a simply increasing curve (+) in the range 700 to 205 nm and displays no Cotton effect.

Elemental analysis Calcd. for $C_{20}H_{41}N_5O_{13}S\cdot 2H_2O$: C 38.3, H 7.23, N 11.17, S 5.12%. Found: C 37.88, H 6.81, N 11.13, S 5.21%.

In thin layer chromatography on silica gel (available under trade name "ART 5721" from Merk Co., Germany), the compound exhibited Rf=0.22 and $R_{kanamycin\ A}$=1.18 when using n-BuOH-MeOH-CHCl$_3$-conc. aqueous $NH_3$ (4:5:2:5) as the developing solvent, as well as Rf=0.17 and $R_{kanamycin\ A}$=1.29 when using n-BuOH-EtOH-CHCl$_3$-17% aqueous NH$_3$ (4:5:2:5).

When the compound was subjected to hydrolysis in 6N hydrochloric acid at 100° C. for one hour, the hydrolysis product was detected as a main spot at Rf=0.35 in thin layer chromatography on silica gel developed with n-BuOH-MeOH-CHCl$_3$-conc. aqueous NH$_3$ (4:5:2:5), this Rf value being identical to that of authentic N-(2-aminoethanesulfonyl)-2-deoxystreptamine and different from that of 2-deoxystreptamine.

Intravenous Injection of 1-N-(2-aminoethanesulfonyl) kanamycin A into mice at a dose of 400 mg/kg killed no mice.

EXAMPLE 2

Following the same procedure as described in Example 1, 2900 mg (6.38 milimoles) of ribostamycin (free base) was reacted with 3300 mg (13.7 milimoles) of N-trifluoroacetyltaurine chloride followed by the removal of the trifluoroacetyl group from the sulfonylated products with conc. aqueous ammonia. Approximately 130 ml of the resulting reaction solution was directly passed through a column of 150 ml of Dowex 1×2 (OH$^-$ form). The column was eluted with water to give eluate fraction Nos. 1–120 and then with 0.1% aqueous acetic acid to give fraction Nos. 121–320, each fraction being collected in 15 ml volume. The fraction Nos. 42–93 contained about 1.8 g of unreacted ribostamycin, while the fraction Nos. 246–306 together contained about 1.0 g of a mixture of N-(2-aminoethanesulfonyl) derivatives of ribostamycin and free taurine resulting from the taurine chloride reactant which was recovered as solid by concentration to dryness. The resulting mixed N-(2-aminoethanesulfonylated) ribostamycins including the desired product were taken up in 20 ml of water and then the solution was passed through a column of 100 ml of Amberlite CG 50 (NH$_4$$^+$form, pH 9–10). The column was eluted with water to give eluate fraction Nos. 1–24 and then with conc. ammonia-water (1:250) mixture to give fraction Nos. 25–76, each fraction being collected in 15 ml volume. The fraction Nos. 65–75 were combined together and concentrated to dryness to afford 382 mg of a primary crude product as powder.

This crude product was taken up in 20 ml of water, followed by passage of the solution through a column of 20 ml of Amberlite CG 50 (NH$_4$$^+$ form, pH 9–10). The column was eluted with water to give eluate fraction Nos. 1–49 and then with conc. ammonia-water (1:300) to give fraction Nos. 50–132, each fraction being collected in 3 ml volume. The fraction Nos. 99–119 were combined together and concentrated to dryness to afford 136.8 mg of a secondary crude product. This product was taken up in 5 ml of water and then passed through a column of 21 ml of Amberlite CG 50 (NH$_4$$^+$ form, pH 9–10). The column was again eluted with water and then with conc. ammoniawater (1:400) to give fraction Nos. 1–37 and Nos. 38–183, respectively, with each fraction being collected in 3 ml volume. The fraction Nos. 122–140 were combined and concentrated to dryness to afford 68.32 mg of a tertiary crude product.

This product was dissolved in 30 ml of water and passed through a column of 10 ml of Dowex 1×2 (OH$^-$ form), followed by elution with water and then with 0.05% aqueous acetic acid to give eluate fraction Nos. 1–11 and Nos. 12–102, respectively, with each fraction being collected in 9 ml volume. The fraction Nos. 80–86 were combined and concentrated to dryness to obtain 44.77 mg of 1-N-(2-aminoethanesulfonyl) ribostamycin. By similar operations, 29.39 mg of further 1-N-(2-aminoethanesulfonyl) ribostamycin was obtained from the fore-cut and tail-cut fractions in each of the elution phases. Total yield 74.16 mg (0.132 milimoles, 2.08%).

1-N-(2-aminoethanesulfonyl) ribostamycin, which is in the form of a colorless powder, has no definite melting point but decomposes and blackens at a temperature of 157°–218° C. This compound shows an optical rotation of $[\alpha]_D^{23}$ = +31° (c=0.58 in water) and its rotatory dispersion gives a simply increasing curve (+) in the range 700 to 205 nm and displays no Cotton effect.

Elementaal analysis Calcd. for C$_{19}$H$_{39}$N$_5$O$_{12}$S.H$_2$O: C 39.4, H 7.08, N 12.1%. Found: C 39.09, H 7.19, N 11.39%.

In thin layer chromatography on silica gel (available under trade name "ART 5721" from Merch Co.,), the compound exhibited Rf=0.25 and $R_{ribostamycin}$=1.21) when using n-BuOH-MeOH-CHCl$_3$-conc. aqueous NH$_3$ (4:5:2:5) as the developing solvent, as well as Rf=0.15 and $R_{ribostamycin}$=1.24 when using n-BuOH-EtOH-CHCl$_3$-17% aqueous NH$_3$ (4:5:2:5).

When tetra-N-acetyl-1-N-(2-aminoethanesulfonyl) ribostamycin was subjected to hydrolysis in 6N hydrochloric acid at 100° C. for one hour, the hydrolysis product was detected as a main spot at Rf=0.37 in thin layer chromatography on silica gel developed with n-BuOH-MeOH-CHCl$_3$-conc. aqueous NH$_3$ (4:5:2:5), this Rf value being identical to that of authentic N-(2-aminoethanesulfonyl)-2-deoxystreptamine and different from that of 2-deoxystreptamine.

Intravenous injection of 1-N-(2-aminoethanesulfonyl) ribostamycin into mice at a dose of 800 mg/kg killed no mice.

EXAMPLE 3

(a) 17.25 g (38.0 millimoles) of ribostamycin (free base) was dissolved in a mixture of 47.5 ml of water and 47.5 ml of dimethylformamide, to which was then added 8.34 ml (60 milimoles) of triethylamine. The mixture was retained at a temperature of 0°–5° C. with ice cooling under agitation, whereupon an ice-cooled solution of 19.65 g (82.0 milimoles) of N-trifluoroacetyltaurine chloride in 65.5 ml of dimethylformamide was added dropwise under vigorous stirring over a period of 25 minutes. The stirring was continued at a temperature of 0°–5° C. for 5 additional minutes and then at room temperature fro 17 hours, followed by addition of 475 ml of water to decompose the remaining reagents. The resultant reaction solution indicated pH 5.6–5.8.

71 ml of conc. aqueous ammonia was added to the reaction solution and the mixture was warmed on a water bath at 70° C. during one hour to effect the removal of the trifluoroacetyl group. After the reaction was completed, the reaction solution was directly passed through a column of 300 ml of Dowex 1×2 (OH$^-$ form). The desired product and unreacted ribostamycin were not adsorbed by the resin column but passed through the column away into the effluent and the water washings, which were then combined together and concentrated to dryness to yield 35.17 g of a crude product. The product was taken up in 125 ml of water and the solution was again passed through a second column of 300 ml of Dowex 1×2 (OH$^-$ form). The column was eluted with water to provide eluate fraction Nos. 1–4 and then with 0.2% aqueous acetic acid to provide fraction Nos. 5–9, each of these fractions being collected in the following volume: Fraction No. 1 (154 ml), No. 2 (220 ml), No. 3 (500 ml), No. 4 (340 ml), No. 5 (660 ml), No. 6 (330 ml), No. 7 (265 ml), No. 8 (265 ml), No. 9 (218 ml). Mixed N-(2-aminoethane sulfonyl) derivatives of ribostamycin were mainly extracted out into the fraction Nos. 4–9, which were combined together and concentrated to dryness to yield a first crop comprising 7.05 g of the crude mixed N-(2-aminoethanesulfonyl) derivatives of ribostamycin.

Unreacted ribostamycin together with a portion of the ribostamycin derivatives containing the desired product was extracted out into the Fraction Nos. 2 and 3, which were combined and passed through a third column of 300 ml of Dowex 1×2 (OH$^{31}$ form). The column was eluted with water to provide eluate fraction Nos. 1–9 and then with 0.2% aqueous acetic acid to provide fraction Nos. 10–22, each of these fractions being collected in the following volume: Fraction No. 1 (150 ml), No. 2 (180 ml), No. 3 (184 ml), No. 4 (180 ml), No. 5 (150 ml), No. 6 (215 ml), No. 7 (365 ml), No. 8 (530 ml), No. 9 (240 ml), No. 10 (400 ml), No. 11 (440 ml), No. 12 (308 ml), No. 13 (406 ml), No. 14 (350 ml), No. 15 (390 ml), No. 16 (350 ml), No. 17 (370 ml), No. 18 (260 ml), No. 19 (270 ml), No. 20 (400 ml), No. 21 (310 ml), No. 22 (640 ml). The fraction Nos. 20–22 were combined together and concentrated to dryness to afford a second crop comprising 7.16 g of crude mixed N-(2-aminoethanesulfonyl) derivatives of ribostamycin. The second crop was combined with the above first crop to yield 14.21 g of the crude, mixed sulfonylated products.

(b) 24.45 g of the crude, mixed sulfonylated products obtained in the above (a) were dissolved in 1.5 l of water and the solution was passed through a column of 200 ml of Amberlite CG 50 (NH$_4^+$ form, pH=c.a.8). The column was eluted with water to provide eluate fraction Nos. 1–6 and then with water-conc. aqueous ammonia (400:1) to provide fraction Nos. 7–10, each of these fractions being collected in the volume indicated below: Fraction No. 1 (100 ml), No. 2 (360 ml), No. 3 (385 ml), No. 4 (310 ml), No. 5 (550 ml), No. 6 (445 ml), No. 7 (350 ml), No. 8 (395 ml), No. 9 (480 ml), No. 10 (385 ml).

Subsequently the following fractions were taken by using a conventional fraction collector and were renumbered wherein the eluate fraction Nos. 1–1060 were collector each in 15 ml volume using as the developing solvent successively mixtures of water and conc. aqueous ammonia in varying ratios of: 400:1 for fraction Nos. 1–742, 300:1 for Nos. 743–780, 200:1 for Nos. 781–1035, 100:1 for Nos. 1036–1063 and 30:1 for No. 1064, with the proviso that the volumes of the fraction Nos. 1061, 1062, 1063 and 1064 were 160 ml, 155 ml, 110 ml and 310 ml, respectively. The fraction Nos. 921–1000 were combined together and concentrated to dryness to yield 829.51 mg (1.48 milimols, 2.2%) of 1-N-(2-aminoethanesulfonyl) ribostamycin.

(c) 759.68 mg (1.312 milimols) of the product, 1-N-(2-aminoethanesulfonyl) ribostamycin obtained in the above (b) was taken up in 15 ml of water, to which was then added 2.62 ml (1.31 milimoles) of 1N sulfuric acid (F=1.0002). The resultant solution presented pH 6.6, which was filtered through glass filter No. 4. The filter was then washed with several volumes of water. The filtrate was combined with the aqueous washings and evaporated to dryness.

There was thus obtained 798.08 mg (1.21 millimoles) of 1-N-(2-aminoethanesulfonyl) ribostamycin monosulfate. Yield 92.4%.

1-N-(2-aminoethanesulfonyl) ribostamycin monosulfate, which is in the form of a colorless powder, has no definite melting point and decomposes gradually at temperatures of 180°–225° C.

Elemental analysis: Calcd. for $C_{19}H_{41}N_5O_{16}S_2 \cdot 2H_2O$: C 32.8% H 6.47% N 10.06% S 9.21%. Found: C 31.75% H 5.80% N 9.72% S 9.97%.

Intravenous injection of 1-N-(2-aminoethanesulfonyl) ribostamycin monosulfate into mice at a dose of 400 mg/kg killed no mice.

EXAMPLE 4

Following the procedure as described in Example 1, 1347.16 mg (2.79 milimoles) of kanamycin B (free base) was reacted with 1504 mg (6.27 milimoles) of N-trifluoroacetyltaurine chloride in a mixture of water and dimethylformamide.

The resultant reaction solution (pH 7.0) was admixed with 6 ml of conc. aqueous ammonia and warmed on a water bath at 70° C. for 2 hours to effect the removal of the trifluoroacetyl group. The solution was then concentrated to dryness, the residue was redissolved in 35 ml of water and the solution obtained was pssed through a column of 100 ml of Dowex 1×2 (OH$^{--}$ form). The column was eluted with water to give eluate fraction Nos. 1–2 and then with 0.2% aqueous acetic acid to give fraction Nos. 3–6, each of these fractions being collected in the following volume: Fraction No. 1 (310 ml), No. 2 (425 ml), No. 3 (255 ml), No. 4 (110 ml), No. 5 (380 ml) and No. 6 (275 ml). The fraction No. 1 contained unreacted kanamycin B (0.51 g), while the fraction No. 5 contained the reaction products and free taurine resulting from the taurine chloride reactant in a total quantity of 1.21 g. The fraction No. 5 was concentrated to dryness, the residue obtained was dissolved in 20 ml of water and the solution passed through a column of 20 ml of Amberlite CG 50 (NH$_4^+$ form, pH 8). The column was eluted successively with water for eluate fraction Nos. 1–3 and with mixtures of conc, aqueous ammonia and water in varying ratios of 1:400 for fraction Nos. 4–28, 1:200 for Nos. 29–98, 1:100 for Nos. 99–120 and 1:25 for Nos. 121–140. The fraction Nos. 1–28 were collected each in 18 ml volume and the fraction Nos. 29–140 collected each in 9 ml volume. The fraction Nos. 77–103 were combined together and concentrated to dryness to yield 110 mg of a primary crude powder of 1-N-(2aminoethanesulfonyl) kanamycin B.

This crude powder was taken up in 70 ml of water and the solution was again passed through a column of 10 ml of Amberlite CG 50 (NH$_4^+$, pH 8). The column was eluted with water to give eluate fraction Nos. 1–9 and then with conc. aqueous ammonia-water (1:150) to give fraction Nos. 10–60, each of the fraction Nos. 1–8 and the fraction Nos. 9–78 being collected in the volume of 18 ml and 6 ml, respectively. The fraction Nos. 16–36 were combined together and concentrated to dryness to yield 100–84 mg of a secondary crude powder of 1-N-(2-aminoethanesulfonyl) kanamycin B.

The secondary crude powder was dissolved in 15 ml of water, followed by passage through a column of 10.5 ml of Dowex 1×2 (OH$^-$ form). The elution of the column was effected with water for eluate fraction Nos. 1–2 and then with 0.05% aqueous acetic acid for fraction Nos. 3–62, with each of these fractions being collected in the following volume: fraction Nos. 1–5 (18 ml), Nos. 6–7 (23 ml), Nos. 8–15 (18 ml), No. 16 (3 ml), Nos. 17–18 (2 ml), Nos. 19–20 (18 ml) and Nos. 21–62 (6 ml). The concentration to dryness of the fraction Nos. 38–56 combined together yielded approx. 100 mg of a tertiary crude powder.

The tertiary crude powder was taken up in 3 ml of a mixture of ethanol-chloroform-conc. aqueous ammonia (4:1:2) and the solution was passed through a column of silica gel (prepared from 21 g of Wakogel C-200 suspended in ethanol-chloroform-conc. aqueous ammonia (4:1:2) mixture). The column was then eluted with said solvent mixture and the eluate collected in 6 ml fractions. The fraction Nos. 16–25 were combined together and concentrated to dryness to yield 66.13 mg of a quaternary crude powder.

The powder obtained was again dissolved in 3 ml of the same solvent mixture as above and chromatographed in columns each of 21 g of the silica gel in the same manner just as above. The fraction Nos. 15–20 of each 6 ml volume obtained from the eluate were combined together and concentrated to dryness to yield 42.73 mg (0.0724 milimoles) of 1-N-(2-aminoethanesulfonyl) kanamycin B. Overall yield 2.59%.

1-N-(2aminoethanesulfonyl) kanamycin B, which is in the form of a colorless powder, has no definite melting point but decomposes and blackens at temperatures of 150°–250° C. This compound shows an optical rotation of $[\alpha]_D^{23} = +117°$ (c=0.35 in water) and its rotatory dispersion gives a simply increasing curve (+) in the range 700 to 205 nm and displays no Cotton effect.

Elemental analysis Calcd. for $C_{20}H_{42}N_6O_{12}S \cdot 2H_2O$: C 38.4% H 7.36% N 13.4%, Found: C 37.76% H 7.05% N 12.70%, In thin layer chromatography on silica gel (available under trade name "Art 5721" from Merk Co.), the compound exhibited Rf=0.24 and $R_{kanamycin\ B}$=1.10 when using n-BuOH-MeOH-CHCl$_3$-conc. aqueous NH$_3$ (4:5:2:5) as the developing solvent, as well as Rf=0.13 and $R_{kanamycin\ B}$=1.18 when using EtOH-CHCl$_3$-conc. aqueous NH$_3$ (4:1:2).

This product was N-acylated with acetic anhydride to prepare penta-N-acetyl-1-N-(2-aminoethanesulfonyl) kanamycin B which was then subjected to hydrolysis in 6N hydrochloric acid at 100° C. for one hour. The hydrolysis product so obtained gave a main spot at Rf=0.37 in thin layer chromatography on silica gel developed with n-BuOH-MeOH-CHCl$_3$-conc. aqueous NH$_3$ (4:5:2:5), this Rf value being identical to that of authentic N-(2-aminoethanesulfonyl)-2-deoxystreptamine and different from that of 2-deoxystreptamine.

EXAMPLE 5

1342.88 mg (3.07 milimoles) of 3'-deoxyribostamycin was dissolved in a mixture of 4 ml of water and 3 ml of dimethylformamide, to which was then added 0.7 ml (5.05 milimoles) of triethylamine. The mixture was retained at a temperature of 0°–5° C. with ice cooling under agitation, whereupon an ice-cooled solution of 1500 mg (6.25 milimoles) of N-trifluoroacetyltaurine chloride in 5 ml of dimethylformamide was added dropwise under vigorous stirring over a period of about six minutes. The stirring was continued at a temperature of 0°–5° C. for one additional hour and then at room temperature for 16 hours, followed by the addition of 40 ml of water to decompose the remaining reagents. The resultant reaction solution presented pH 7.0.

.6 ml of conc. aqueous ammonia was added to the reaction solution and the mixture was warmed on a water bath at 70° C. during for 2 hours to effect the removal of the trifluoroacetyl group from the product. After the reaction was completed, the reaction solution was concentrated to dryness and the residue was taken up in 35 ml of water, followed by passage through a column of 100 ml of Dowex 1×2 (OH$^-$ form). The column was eluted with water to give eluate fraction Nos. 1–2 and then with 0.2% aqueous acetic acid to give fraction Nos. 3–5, each of these fractions being collected in the following volume: fraction No. 1 (450 ml), No. 2 (390 ml), No. 3 (415 ml), No. 4 (400 ml) and No. 5 (150 ml). 520 mg of unreacted 3'-deoxyribostamycin was recovered from the fraction No. 1, while the fraction Nos. 3 and 4 contained the required, mixed N-(2-aminoethanesulfonyl) derivatives of 3'-deoxyribostamycin and part of free taurine resulting from the taurine chloride reactant in a total quantity of 1670 mg.

The fraction Nos. 3–4 combined together was concentrated to dryness and the residue so obtained containing the desired product was taken up in 40 ml of water and then the solution was passed through a column of 20 ml of Amberlite CG 50 (NH$_4^{30}$ form, pH 8). The column was eluted successively with water for eluate fraction Nos. 1–3 and with mixtures of conc. aqueous ammonia-water in varying ratios of 1:400 for fraction Nos. 4–27, 1:200 for Nos. 28–73, 1:100 for Nos. 74–96, 1:50 for Nos. 97–107 and 1:25 for Nos. 108–120, the fraction Nos. 1–27 and Nos. 28–120 each being collected in the volume of 18 ml and each 9ml. respectively. The fraction Nos. 81–93 were combined together and concentrated to dryness to yield 87.83 mg of a crude product of 1-N-(2-aminoethanesulfonyl)-3'-deoxyribostamycin.

This crude product was dissolved in 7 ml of a solvent mixture of ethanol-chloroform-conc. aqueous ammonia (4:1:2) and the solution was passed through a column of 25 g of silica gel (Wakogel c-200which had been impregnated with said solvent mixture. The column was then eluted with said solvent mixture and the eluate was collected in 6 ml fractions. The fraction Nos. 22–31 were combined together and concentrated to dryness to yield 67.98 mg (0.125 millimoles, 4.06%) of 1-N-(2-aminoethanesulfonyl)-3'-deoxyribostamycin.

1-N-(2-aminoethanesulfonyl)-3'-deoxy- ribostamycin, which is in the form of colorless powder, has no definite melting point and decomposes gradually at temperatures of 150°–225° C.

Elemental analysis Calcd. for $C_{19}H_{39}N_5O_{11}S \cdot 3H_2O$: C 38.1% H 7.5% N 11.7%. Found: C 36.98% H 6.46% N 11.21%.

In thin layer chromatography on silica gel (available under trade name "ART 5721" from Merch Co.), the compound exhibited Rf=0.33 and R$_{3'}$-deoxyribostamcin=1.18 when using n-BuOH-MeOH-CHCl$_3$-conc. aqueous NH$_3$ (4:5:2:5) as the developing solvent, as well as Rf=0.22 and R$_{3'\text{-}deoxyribostamycin}$=1.30 when using EtOH-CHCl$_3$- aqueous NH$_3$ (4:1:2).

EXAMPLE 6

Following the same procedure as described in Example 5, 1268 mg (2.81 milimoles) of dibekacin (ie. 3',4'-dideoxykanamycin B) was allowed to react with 1502 mg (6.27 milimoles) of trifluoroacetyltaurine chloride in a mixture of water and dimethylformamide in the presence of triethylamine, followed by the removal of trifluoroacetyl group from the reaction product by treating with conc. aqueous ammonia.

The resultant reaction solution was concentrated to dryness and the residue was taken up in 35 ml of water, followed by passage through a column of 100 ml of Dowex 1×2 (OH⁻form). The column was eluted with water to give eluate fraction Nos. 1-2 and then with 0.2% aqueous acetic acid to give fraction Nos. 3-6, each of these fractions being collected in the following volume: fraction No. 1 (340ml), No. 2 (400ml), No. 3 (400ml), No. 4 (300ml), No. 5 (200ml) and No. 6 (300ml). 569 mg of unreacted dibekacin was recovered from the fraction No. 1, while the fraction No. 4 contained the required mixed N-(2-aminoethanesulfonyl) derivatives of dibekacin and part of free taurine resulting from the taurine chloride reactant in a total quantity of 900mg.

The fraction No. 4 was concentrated to dryness and the residue containing the desired product was dissolved in 20 ml of water and then passed through a column of 20 ml of Amberlite CG 50 (NH$_4$⁺form, pH 8). The column was eluted successively with water for eluate fraction Nos. 1-4 and with mixtures of conc. aqueous ammonia-water in different ratios of 1:400 for fraction Nos. 5-28, 1:200 for Nos. 29-165, 1:100 for Nos. 166-211 and 1:30 for Nos. 212-233, the fraction Nos. 1-34 and Nos. 35-233 being collected in the volumes of 18 ml and 9 ml, respectively. The fraction Nos. 169-183 were combined together and concentrated to dryness to yield 54.26 mg of a crude product of 1-N-(2aminoethanesulfonyl) dibekacin.

40 mg of the crude product was dissolved in 6 ml of a solvent mixture of ethanol-chloroform-conc. aqueous ammonia (4:1:1) and the solution was passed through a column of 25 g of silica gel (Wakogel C-200) which had been impregnated with said solvent mixture. The column was then eluted with said solvent mixture and the eluate was collected in 6 ml fractions. The fraction Nos. 62-80 were combined together and concentrated to dryness to yield 23.84 mg (0.0428 milimoles, yield 2.06%) of 1-N-(2aminoethanesulfonyl) dibekacin.

1-N-(2-aminoethanesulfonyl) dibeckacin, which is in the form of colorless powder, has no definite melting point and decomposes gradually at temperatures of 130°-210° C.

In thin layer chromatography on silica gel (of the same grade as mentioned above), the compound exhibited $R_f=0.42$ and $R_{dibekacin}=1.08$ when using n-BuOH-MeOH-CHCl$_3$-conc. aqueous NH$_3$ (4:5:2:5) as the developing solvent, as well as $R_f=0.28$ and $R_{dibekacin}=1.13$ when using EtOH-CHCl$_3$-conc. NH$_3$ (4:1:2).

This product was acetylated by treating with acetic anhydride to give penta-N-acetyl-1-N-(2-aminoethanesulfonyl) dibekacin which was then subjected to hydrolysis in 6N hydrochloric acid at 100° C. for one hour. The hydrolysis product so obtained gave a main spot at $R_f=0.37$ in thin layer chromatography on silica gel developed with n-BuOH-MeOH-CHCl$_3$-conc. NH$_3$ (4:5:2:5), this $R_f$ value being identical to that of authentic N-(2-aminoethanesulfonyl)-2-deoxystreptamine and different from that of 2-deoxystreptamine.

EXAMPLE 7

Following the same procedure as described in Example 5, 715 mg (1.695 millimoles) of 3',4'-dideoxyribostamycin was allowed to react with 840 mg (3.53 millimoles) of trifluoroacetyltaurine chloride in a mixture of water and dimethylformamide, followed by the removal of trifluoroacetyl group from the reaction product by treating with conc. aqueous ammonia.

The resultant reaction solution was concentrated to dryness and the solid residue was taken up in 30 ml of water, followed by passage of the solution through a column of 70 ml of Dowex 1×2 (OH⁻ form). The column was eluted with water to provide eluate fraction Nos. 1-2 and then with 0.2% aqueous acetic acid to provide fraction Nos. 3-4, each of these fractions being collected in the following volume: fraction No. 1 (300ml), No. 2 (225ml), No. 3 (285ml) and No. 4 (320ml). The fraction No. 1 contained 300mg of unreacted 3',4'-dideoxyribostamycin, while the fraction No. 4 was concentrated to dryness to yield a solid residue comprising the mixed N-(2-aminoethanesulfonyl) derivatives of 3',4'-dideoxyribostamycin and part of taurine resulting from the taurine chloride reactant. Yield 1040 mg.

The solid residue containing the desired product was dissolved in 20 ml of water and then the solution passed through a column of 16 ml of Amberlite CG 50 (NH$_4$⁺ form, pH 8). The column was eluted successively with water for eluate fraction Nos. 1-2 and with mixtures of conc. aqueous ammonia and water in varying ratios of 1:400 for fraction Nos. 3-27, 1:200 for Nos. 28-72, 1:100 for Nos. 73-94, 1:50 for Nos. 95-107 and 1:25 for Nos. 108-117, the fraction Nos. 1-27 and Nos. 28-117 being collected in the volume of 18 ml and 9 ml, respectively. The fraction Nos. 95-102 were combined together and concentrated to dryness to yield 47.20 mg of a crude product of 1-N-(2-aminoethanesulfonyl)-3',4'-dideoxyribostamycin.

This crude product was dissolved in 18 ml of a solvent mixture of ethanol-chloroform-conc. aqueous ammonia (4:1:1.2) and the solution was passed through a column of 25 g of silica gel (Wakogel C-200) which had been impregnated with said solvent mixture. The column was then eluted with said solvent mixture and the eluate was collected in fractions of 9 ml. The fraction Nos. 33-59 were combined together and concentrated to dryness to yield 44.09 mg (0.083 millimoles) of 1-N-(2-aminoethanesulfonyl)-3',4'-dideoxyribostamycin. Yield 4.9%.

1-N-(2-aminoethanesulfonyl)-3',4'-dideoxyribostamycin, which is in the form of colorless powder, has no definite melting point and decomposes gradually at temperatures of 140°-175° C.

In thin layer chromatography on silica gel (the same as mentioned just above), the compound exhibited $R_f=0.42$ and $R_{3',4'-dideoxyribostamycin}1.2$ when using n-BuOD-MeOH-CHCl$_3$-conc.aqueous NH$_3$ (4:5:2:5) as the developing agent, as well as $R_f=0.33$ and $R_{3',4'-dideoxyribostamycin}=1.28$ when using EtOH-CHCl$_3$-conc. NH$_3$ (4:1:2).

The above product was reacted with acetic anhydride to prepare tetra-N-acetyl-1-N-(2-aminoethanesulfonyl)-3',4'-dideoxyribostamycin. This compound was subjected to hydrolysis in 6N hydrochloric acid at 100° C. for one hour, and the hydrolysis product so obtained gave a main spot at $R_f=0.37$ in thin layer chromatography on silica gel developed with n-BuOH-MeOH-CHCl$_3$-conc. NH$_3$ (4:5:2:5), this $R_f$ value being identical to that of authentic N-(2-aminoethanesulfonyl)-2-deoxystreptamine and different from that of 2-deoxystreptamine.

EXAMPLE 8

Following the same procedure as described in Example 5, 804 mg (1.724 milimoles) of 3'-deoxykanamycin B was allowed to react with 1000 mg (4.20 milimoles) of trifluoroacetyltaurine chloride in a mixture of water and dimethylformamide, followed by the removal of the trifluoroacetyl group from the reaction product by treating with conc. aqueous ammonia.

The resultant reaction solution was concentrated to dryness and the solid residue was taken up in 30 ml of water, followed by passage of the solution through a column of 80 ml of Dowex 1×2 (OH⁻ form). The column was eluted with water to provide eluate fraction Nos. 1–2 and then with 0.2% aqueous acetic acid to provide fraction Nos. 3–4, each of these fractions being collected in the following volume: fraction No. 1 (265ml), No. 2 (195ml), No. 3 (290ml), and No. 4 (310ml). The fraction No. 1 contained 480 mg of unreacted 3'-deoxykanamycin B, while the fraction No. 4 was concentrated to dryness to yield a solid residue comprising the mixed N-(2-aminoethanesulfonyl) derivatives of 3'-deoxykanamycin B and part of taurine resulting from the taurine chloride reactant in a total quantity of 900 mg.

The solid residue containing the desired product was dissolved in 20 ml of water and then the solution passed through a column of 16 ml of Amberlite CG 50 (NH⁺ form, pH 8). The column was eluted successively with water for eluate fraction Nos. 1–3 and with mixtures of conc. aqueous ammonia and water in varying ratios of 1:400 for fraction Nos. 4–28, 1:200 for Nos. 29–73, 1:100 for Nos 74–95, 1:50 for Nos. 96–106 and 1:25 for Nos. 107–114, the fraction Nos. 1–28 and Nos. 29–114 being collected in the volume of 18 ml and 9 ml, respectively. The fraction Nos. 74–76 were combined together and concentrated to dryness to yield 41.26mg of a crude product of 1-N-(2-aminoethanesulfonyl)-3'-deoxykanamycin B.

This crude product was dissolved in 27 ml of a solvent mixture of ethanol-chloroform-conc. aqueous ammonia (4:1:1.2) and the solution was passed through a column of 25 g of silica gel (Wakogel C-200) which has been impregnated with said solvent mixture. The column was then eluted with said solvent mixture and the eluate was collected in fractions of each 9 ml. The fraction Nos. 51–67 were combined together and concentrated to dryness to yield 23.74 mg (0.041 millimoles), of 1-N-(2-aminoethanesulfonyl)-3'-deoxykanamycin B. Yield 2.4%.

1-N-(2-aminoethanesulfonyl)-3'-deoxykanamycin B, which is in the form of colorless powder, has no definite melting point and decomposes gradually at temperatures of 140°–211° C.

In thin layer chromatography on silica gel (the same as mentioned just above), the compound exhibited $R_f$—0.32 and $R_{3'-deoxykanamycin\ B}$=1.13 when using n-BuOH-MeOH-CHCl₃-conc. NH₃ (4:5:2:5) as the developing agent, as well as $R_f$=0.26 and $R_{3'-deoxykanamycin}$=1.20 when using EtOH-CHCl₃-conc. NH₃ (4:1:2).

When penta-N-acetyl-1-N-(2-aminoethanesulfonyl)-3'-deoxykanamycin B which was obtained by acetylation of the above product was subjected to hydrolysis in 6N hydrochloric acid at 100° C. for one hour, the hydrolysis product gave a main spot at $R_f$=0.37 in thin layer chromatography on silic gel developed with n-BuOH-MeOH-CHCl₃-conc. NH₃ (4:5:2:5), this $R_f$ value being identical to that of authentic N-(2-aminoethanesulfonyl)-2-deoxystreptamine and different from that of 2-deoxystreptamine.

EXAMPLE 9

1187 mg (2.455 millimoles) of kanamycin B (free base) was dissolved in a mixture of 3ml of water and 3 ml of dimethylformamide, to which was then added 0.42ml (3.03 millimoles) of triethylamine. The mixture was retained at a temperature of 0°–5° C. with ice-cooling under agitation, whereupon an ice-cooled solution of 1410 mg (5.59 millimoles) of trifluoroacetyl-3-aminopropanesulfonyl chloride in 4.7 ml of dimethylformamide was added dropwise under vigorous stirring over a period of 7 minutes. The stirring was continued at a temperature of 0°–5° C. for an additional half an hour and then at room temperature for 17 hours, followed by addition of 90 ml of water to decompose the remaining reagents. The resultant reaction solution presented pH 3.0.

6 ml of conc. aqueous ammonia was added to the reaction solution and the mixture was warmed on a water bath at 70° C. for one hour to remove the trifluoroacetyl group from the reaction product. After the reaction was completed, the resultant reaction solution was concentrated to dryness and the solid residue was taken up in 35 ml of water, followed by passage of the solution through a column of 100 ml of Dowex 1×2 (OH⁻ form). The column was eluted with water to provide eluate fraction Nos. 1–2 and then with 0.2% aqueous acetic acid to provide fraction Nos. 3–6, each of these fractions being collected in the following volume: fraction No. 1 (370 ml), No. 2 (450 ml), No. 3 (300ml), No. 4 (250ml), No. 5 (120ml) and No. 6 (330ml). The fraction No. 1 contained 530 mg of unreacted kanamycin B. The fraction Nos. 2–4 were combined together and concentrated to dryness to yield a solid residue comprising n-(3-aminopropanesulfonyl) derivatives of kanamycin B and 3-aminopropane sulfonic acid resulting from the sulfonyl chloride reactant. Yield 13201320

The solid residue containing the desired product was taken up in 40 ml of water and then the solution passed through a column of 20ml of Amberlite CG (NH₄⁺ form, pH 8). The column was eluted successively with water for eluate fraction Nos. 1–3 and with mixtures of conc. aqueous ammonia and water mixtures in varying ratios of 1:400 for fraction Nos. 4–26, 1:200 for Nos. 27–73, 1:100 for Nos. 74–115, 1.50 for Nos. 116–134 and 1:25 for Nos. 135–146, the fraction Nos. 1–26 and Nos. 27–147 being collected in the volumes of 18 ml and 9 ml, respectively. The fraction Nos. 101–119 were combined together and concentrated to dryness to yield 62.68 mg of a crude product of 1-N-(3-aminopropanesulfonyl) kanamycin B.

This crude product was dissolved in 6 ml of a solvent mixture of ethanol-chloroform-conc. aqueous ammonia (4:1:2) and the solution was passed through a column of 21 g of silica gel (Wakogel C-200) which had been impregnated with said solvent mixture. The column was then eluted with said solvent mixture and the eluate was collected in fractions of each 6 ml. The fraction Nos. 15–27 were combined together and concentrated to dryness to yield 44.37 mg of a secondary crude product.

The crude product was taken up in 3 ml of water and the solution was again passed through a column of 10 ml of Amberlite CG 50 (NH₄+, pH 8). The column was eluted successively with water for eluate fraction Nos.

1-3 and with mixtures of conc. aqueous ammonia and water in varying ratios of 1:100 for fraction Nos. 4-7, 1:85 for Nos. 8-18, 1:70 for Nos. 19-27 and 1:55 for Nos. 28-34, each of these fractions being collected in the volume of 9 ml. The fractions Nos. 10-22 were combined and concentrated to dryness and the residue was redissolved in 10 ml of water and then the solution passed through a column of 9 ml of Dowex 1×2 (OH⁻). The column was eluted with water to provide eluate fraction Nos. 1-13 and then with 0.05% aqueous acetic acid to provide fraction Nos. 14-46, the fraction Nos. 1-13 and the fraction Nos. 14-46 being collected in the volume of 18 ml and 9 ml, respectively. The fraction Nos. 35-41 were combined together and concentrated to dryness to yield 24.41 mg of a tertiary crude product.

The tertiary crude product was taken up in 6 ml of a solvent mixture of ethanol-chloroform-conc. aqueous ammonia (4:1:2) and the solution was passed through a column of 25 g of silica gel (Wakogel C-200) which had been impregnated with said solvent mixture. The column was then eluted with said solvent mixture and the eluate was collected in fractions of each 6 ml. The fraction Nos. 39-49 were combined together and concentrated to dryness to yield 15.66 mg (0.026 milimoles) of 1-N-(3-aminopropanesulfonyl) kanamycin B. Yield 1.1%.

1-N-(3-aminopropanesulfonyl) kanamycin B which is in the form of colorless powder, has no definite melting point and decomposes gradually at temperatures of 140°-240° C.

In thin layer chromatography on silica gel (the same as mentioned just above), the compound exhibited $R_f=0.19$ and $R_{kanamycin\ B}=0.87$ when using n-BuOH-MeOH-CHCl$_3$-conc. NH$_3$ (4:5:2:5) as the developing agent, as well as $R_f=0.084$ and $R_{kanamycin\ B}=0.74$ when using EtOH-CHCl$_3$-conc. NH$_3$ (4:1:2).

EXAMPLE 10

Following the same procedure as described in Example 9, 1240 mg (2.75 millimoles) of dibekacin (free base) was allowed to react with 1580 mg (6.28 millimoles) of trifluoroacetyl-3-amino-propanesulfonyl chloride in a mixture of water and dimethylformamide in the presence of triethylamine, followed by the removal of the tri-fluoroacetyl group from the reaction product by treating with conc, aqueous ammonia.

The resultant reaction solution was concentrated to dryness and the solid residue was taken up in 40 ml of water, followed by passage of the solution through a column of 70 ml of Dowex 1×2 (OH⁻form). The column was eluted with water to provide eluate fraction Nos. 1-2 and then with 0.2% aqueous acetic acid to provide fraction Nos. 3-6, each of these fractions being collected in the following volumes : fraction No. 1 (300 ml), No. 2 (450 ml), No. 3 (400 ml), No. 4 (300 ml), No, 5 (200 ml) and No. 6 (300 ml). The fraction No. 1 contained 512 mg of unreacted dibekacin. The fraction Nos. 3-5 were combined together and concentrated to dryness to yield a solid residue comprising N-(3-aminopropanesulfonyl) derivatives of dibekacin and 3-aminopropanesulfonic acid resulting from the sulfonyl chloride reactant. Yield 1570 mg.

The solid residue containing the desired product was dissolved in 50 ml of water and then the solution passed through a column of 20 ml of Amberlite CG 50 (NH$_4$' form, pH 8). The column was eluted successively with water for eluate fraction Nos. 1-6 and with mixtures of conc. aqueous ammonia and water in varying ratios of 1:400 for fraction Nos. 7-18, 1:200 for Nos. 19-88, 1:100 for Nos. 89-138, 1:50 for Nos. 139-158 and 1:25 for Nos. 159-169, the fraction Nos. 1-18 and Nos. 19-169 being collected in the volume of 18 ml and 9 ml, respectively. The fraction Nos. 148-156 were combined together and concentrated to dryness to yield 60.7 mg of a crude product of 1-N-(3-aminopropanesulfonyl) dibekacin.

This crude product was dissolved in 30 ml of water and the solution was passed through a column of 11 ml of Dowex 1×2 (OH⁻). The column was eluted with water to provide eluate fraction Nos. 1-3 and then with 0.05% aqueous acetic acid to provide fraction Nos. 4-54, the fraction Nos. 1-19 and fraction Nos. 20-54 being collected in the volumes of 18 ml and 9 ml, respectively. The fraction Nos. 39-45 were combined together and concentrated to dryness to yield 28.21 mg (0.049 millimoles) of 1-N-(3-aminopropanesulfonyl) dibekacin. Yield 1.8%.

1-N-(3-aminopropanesulfonyl) dibekacin, which is in the form of colorless powder, has no definite melting point and decomposes gradually at temperatures of 118°-230° C.

In thin layer chromatography on silica gel (of the same grade as mentioned above), the compound exhibited $R_f=0.32$ and $R_{dibekacin}=0.88$ when using a n-BuOH-MeOH-CHCl$_3$-17% aqueous NH$_3$ (4:5:2:5) as the developing agent, as well as $R_f=0.24$ and $R_{dibekacin}=0.87$ when using n-BuOH-EtOH-CHCl$_3$-17% aqueous NH$_3$ (4:5:2:5).

EXAMPLE 11

485 mg (1.0 millimoles) of kanamcyin A (free base) was suspended in 1 ml of methanol, to which was then added a solution of 0.3 ml (4 millimoles) of trifluoroacetic acid in 2 ml of methanol, resulting in a mixture in the form of clear solution. 0.05 ml (3.6 millimoles) of triethylamine was added to the mixture, followed by dropwise addition, under vigorous stirring at ambient temperature over 5 minutes, of a solution of 0.5 g (2 millimoles) of trifluoroacetyl-3-aminopropanesulfonyl chloride in 2 ml of methanol. The stirring was continued at ambient temperature for further 17 hours and subsequently 60 ml of water was added to decompose the remaining reagents. The resultant reaction solution indicated pH 3.5.

9 ml of conc. aqueous ammonia was added to the reaction solution and the mixture was warmed on a water bath at 70° C. for one hour to remove the trifluoroacetyl group from the product. After the reaction was completed, the reaction solution was concentrated to dryness and the solid residue was taken up in 20 ml of water, followed by passage of the solution through a column of 50 ml of Dowex 1×2 (OH⁻form). The column was eluted with water to provide eluate fraction Nos. 1-2 and then with 0.2% aqueous acetic acid to provide fraction Nos. 3-4, each of these fractions being collected in the following volumes : fraction No. 1 (205 ml), No. 2 (165 ml), No. 3 (195 ml), No. 4 (210 ml). Then, unreacted kanamycin A was extracted to be present in the fraction No. 1, while the mixed N-(3-aminopropanesulfonyl) derivatives of kanamycin A and 3-aminopropane sulfonic acid resulted from the sulfonyl chloride were extracted to be present in the fraction No. 4.

The fraction No. 4 was concentrated to dryness to yield a solid residue. This solid residue containing the desired sulfonylated product was dissolved in 15 ml of water and then the solution was passed through a column of 10 ml of Amberlite CG 50 (NH$_4$+form, pH 8). The column was eluted successively with water for eluate fraction Nos. 1–2 and with mixtures of conc. aqueous ammonia and water in varying ratios of 1:400 for fraction Nos. 3–26, 1:200 for Nos. 27–50, 1:100 for Nos. 51–72 and 1:25 for Nos. 73–101, the fraction Nos. 1–26 and Nos. 27–101 being collected in the volumes of 18 ml and 9 ml, respectively. The fraction Nos. 54–59 were combined together and concentrated to dryness to yield 15.34 mg (0.025 millimoles) of 1-N-(3-amino-propanesulfonyl) kanamycin A. Yield 2.5%.

1-N-(3-aminopropanesulfonyl) kanamycin A, which is in the form of colorless powder, had no definite melting point and decomposes gradually at temperatures of 200°–240° C.

In thin layer chromatography on silica gel (of same grade as mentioned above), the compound exhibited $R_f$=0.16 and $R_{kanamycin\ A}$=0.85 when using n-BuOH-MeOH-CHCl$_3$-17% NH$_3$ (4:5:2:5) as the developing agent, as well as $R_f$=0.10 and $R_{kanamycin\ A}$=0.77 when using EtOH-CHCl$_3$-conc. NH$_3$ (4:1:2).

EXAMPLE 12

Following the procedure similar to that described in Example 11, 484.18 mg (1.0 millimoles) of kanamycin A (free base) was allowed to react with 0.52 g (1.94 millimoles) of trifluoroacetyl-4-aminobutanesulfonyl chloride in methanol, followed by the removal of trifluoroacetyl group from the reaction product by treating the product with conc. aqueous ammonia.

The resultant reaction solution was concentrated to dryness and the solid residue was taken up in 20 ml of water, followed by passage of the solution through a column of 50 ml of Dowex 1×2 (OH$^-$form). The column was eluted with water to provide eluate fraction Nos. 1–2 and then with 0.2% aqueous acetic acid to provide fraction Nos. 3–4, each of these fractions being collected in the following volumes: fraction No. 1 (395 ml), No. 2 (125 ml), No. 3 (225 ml), No. 4 (265 ml). Then, unreacted kanamycin A was extracted to be present in the fraction No. 1, while the mixed N-(4-aminobutanesulfonyl) derivatives of kanamycin A and 4-aminobutanesulfonic acid resulted from the sulfonyl chloride were extracted to be present in the fraction No. 4.

The fraction No. 4 including the desired product was concentrated to dryness, the resulting solid residue was dissolved in 15 ml of water and then the solution was passed through a column of 11 ml of Amberlite CG 50 (NH$_4^{30}$ form, pH 8). The column was eluted successively with water for eluate fraction Nos. 1–4 and with mixtures of conc. aqueous ammonia and water in varying ratios of 1:400 for fraction Nos. 5–29, 1:200 for Nos. 30–75, 1:100 for Nos. 76–100 and 1:25 for Nos. 101–130, the fraction Nos. 1–29 and Nos. 30–130 being collected in the volumes of 18 ml and 9 ml, respectively. The fraction Nos. 100–103 were combined together and concentrated to dryness to yield 10.18 mg (0.016 millimoles) of 1-N-(4-aminobutanesulfonyl) kanamycin A. Yield 1.6%.

1-N-(4-aminobutanesulfonyl) kanamycin A, which is in the form of colorless powder, has no definite melting point and decomposes gradually at temperatures of 162°–240° C.

In thin layer chromatography on silica gel (of same grade as mentioned above), the compound exhibited $R_f$=0.13 and $R_{kanamycin\ A}$=0.70 when using n-BuOH-MeOH-CHCl$_3$-conc. NH$_3$ (4:5:2:5) as the developing agent, as well as $R_f$=0.08 and $R_{kanamycin\ A}$=0.65 when using EtOH-CHCl$_3$-conc. NH$_3$ (4:1:2).

What we claim is:

1. A compound of the formula:

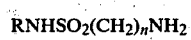

or a pharmaceutically acceptable salt thereof, wherein RNH— represents the residue of an aminoglycosidic antibiotic comprising a 2-deoxystreptamine moiety in its molecule, the nitrogen atom in the residue RNH— being bonded to the carbon atom at the 1-position of the 2-deoxystreptamine moiety, and n represents an integer of 2, 3, or 4.

2. A compound according to claim 1, wherein RNH— represents the residue of ribostamycin having the formula:

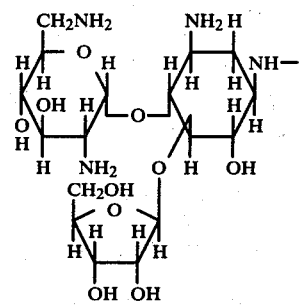

3. A compound according to claim 1, wherein RNH— represents the residue of kanamycin A having the formula:

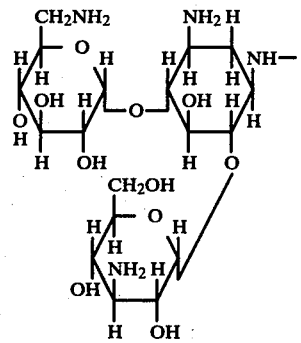

4. A compound according to claim 1, wherein RNH— represents the residue of kanamycin B having the formula:

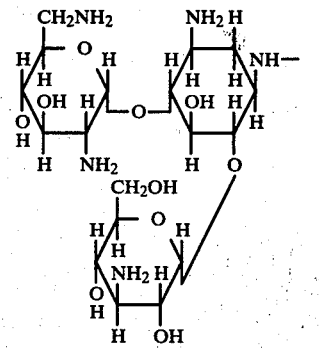

5. A compound according to claim 1, wherein RNH—represents the residue of 3'-deoxyribostamycin having the formula:

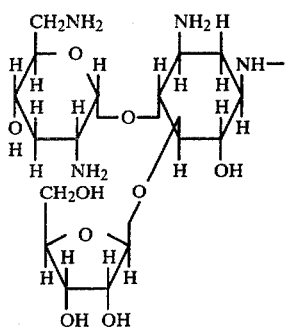

6. A compound according to claim 1, wherein RNH—represents the residue of 3',4'-dideoxykanamycin B having the formula:

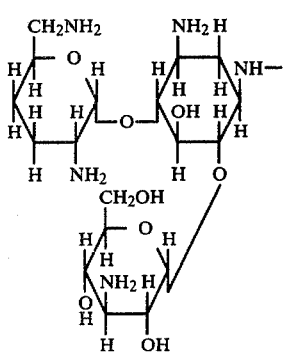

7. A compound according to claim 1, wherein RNH—represents the residue of 3',4'-dideoxyribostamycin having the formula:

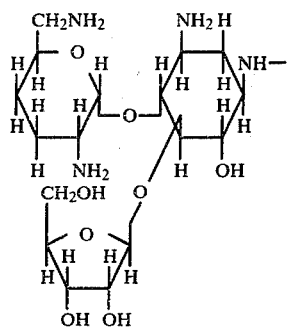

8. A compound according to claim 1, wherein RNH—represents the residue of 3'-deoxykanamycin B having the formula:

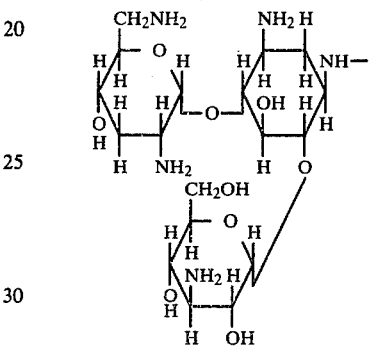

9. A compound according to claim 1, which is selected from the group consisting of
1-N-(3-Aminopropanesulfonyl)-kanamycin A,
1-N-(4-Aminobutanesulfonyl)-kanamycin A,
1-N-(3-Aminopropanesulfonyl)-kanamycin B,
1-N-(2-Aminoethanesulfonyl)-3'-deoxykanamycin B,
1-N-(2-Aminoethanesulfonyl)-3',4'-didecy-kanamycin B
1-N-(3-Aminopropanesulfonyl)-3',4'-didecy-kanamycin B
1-N-(2-Aminoethanesulfonyl)-3'-deoxyribostamycin, and
1-N-(2-Aminoethanesulfonyl)-3',4'-dideoxyribostamycin.

10. A compound according to claim 1, which is
1-N-(2-Aminoethanesulfonyl)-kanamycin A,
1-N-(2-Aminoethanesulfonyl)-kanamycin B or
1-N-(2-Aminoethanesulfonyl)-ribostamycin.

11. An antibacterial composition comprising as the active ingredient an antibacterially effective amount of a 1-N-(ω-aminoalkanesulfonyl) derivative of an aminoglycosidic antibiotic as defined in claim 1, in combination with a pharmaceutically acceptable carrier for the active ingredient.

12. A method of therapeutically treating a susceptible bacterial infection in an animal including humans which comprises administering to the host of the susceptible bacterial infection a safe and antibacterially effective amount of a 1-N-(ω-aminoalkanesulfonyl) derivative of an aminoglycosidic antibiotic as defined in claim 1, to inhibit the growth of bacteria.

* * * * *

UNITED STATES PATENT OFFICE
CERTIFICATE OF CORRECTION

PATENT NO. : 4,170,641
DATED : October 9, 1979
INVENTOR(S) : Eiichi Akita et al.

It is certified that error appears in the above-identified patent and that said Letters Patent are hereby corrected as shown below:

Claim 9, lines 7 to 10, should read as follows:

1-N-(2-Aminoethanesulfonyl)-3',4'-dideoxy-kanamycin B
    1-N-(3-Aminoethanesulfonyl)-3',4'-dideoxy-kanamycin B Signed and Sealed this First Day of January 1980

[SEAL]

Attest:

SIDNEY A. DIAMOND

Attesting Officer      Commissioner of Patents and Trademarks